United States Patent
Cornelius et al.

(12) 
(10) Patent No.: US 6,656,134 B2
(45) Date of Patent: Dec. 2, 2003

(54) GUIDE WIRE WITH HYDROPHILICALLY COATED TIP

(75) Inventors: Richard G. Cornelius, Wayzata, MN (US); Anthony Kelzenberg, Watertown, MN (US); Michael J. Urick, Rogers, MN (US); Brian R. Reynolds, Ramsey, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 2 days.

(21) Appl. No.: 09/874,794

(22) Filed: Jun. 5, 2001

(65) Prior Publication Data

US 2002/0045885 A1 Apr. 18, 2002

Related U.S. Application Data

(63) Continuation of application No. 09/361,881, filed on Jul. 27, 1999, now Pat. No. 6,251,086, which is a continuation of application No. 08/812,750, filed on Mar. 6, 1997, now Pat. No. 5,924,998.

(51) Int. Cl.[7] ............................. A61B 5/00; A61M 25/00
(52) U.S. Cl. ........................................................ 600/585
(58) Field of Search ................................. 600/585, 433, 600/434, 435, 436; 606/213, 159; 604/523

(56) References Cited

U.S. PATENT DOCUMENTS

| | | | |
|---|---|---|---|
| 4,282,876 A | 8/1981 | Flynn | 128/349 R |
| 4,345,602 A | 8/1982 | Yoshimura et al. | 128/349 R |
| 4,456,017 A | 6/1984 | Miles | 128/772 |
| 4,534,363 A | 8/1985 | Gold | 128/772 |
| 4,642,267 A | 2/1987 | Creasy et al. | 428/413 |
| 4,682,607 A | 7/1987 | Vaillancourt et al. | 128/772 |
| 4,721,117 A | 1/1988 | Mar et al. | 128/772 |
| 4,729,914 A | 3/1988 | Kliment et al. | 428/36 |
| 4,739,768 A | 4/1988 | Engelson | 128/658 |

(List continued on next page.)

FOREIGN PATENT DOCUMENTS

| | | |
|---|---|---|
| EP | 0 340 304 A1 | 11/1989 |
| EP | 0 380 102 A1 | 8/1990 |
| EP | 0 395 098 A1 | 10/1990 |
| EP | 0 405 823 A2 | 1/1991 |
| EP | 0 407 965 A1 | 1/1991 |
| EP | 0 519 604 A2 | 12/1992 |
| EP | 0 661 073 A1 | 7/1995 |
| EP | 0 744 186 A1 | 11/1996 |
| FR | 2 401 668 | 8/1977 |
| JP | 60-12069 | 1/1985 |
| JP | 2-180277 | 7/1990 |
| JP | 8-257133 | 10/1996 |
| WO | WO 85/01444 | 4/1985 |
| WO | WO 89/09626 | 10/1989 |
| WO | WO 91/00051 | 1/1991 |
| WO | WO 96/34635 | 11/1996 |

OTHER PUBLICATIONS

Tegtmeyer, "Current Problems in Diagnostic Radiology", vol. XVI, No.2, Mar./Apr., 1987, pp.79–80.

Primary Examiner—Max F. Hindenburg
Assistant Examiner—Brian Szmal
(74) Attorney, Agent, or Firm—Crompton, Seager & Tufte LLC

(57) ABSTRACT

A guide wire including a lubricous distal portion and a less lubricous intermediate portion proximal of said distal portion. One guide wire provides a highly lubricous distal portion with a hydrophilic layer and a less lubricous intermediate portion with a hydrophobic layer. Another guide wire provides a lubricous distal portion with a polymer tip that is itself hydrophilic. Yet another guide wire provides a less lubricous intermediate portion using a stainless steel coil helically wound around the tapering intermediate portion. The coil is preferably coated with a hydrophobic coating such as PTFE or silicone. The coil can either abut the distal portion proximal end or extend into the distal portion interior.

15 Claims, 2 Drawing Sheets

U.S. PATENT DOCUMENTS

| | | | |
|---|---|---|---|
| 4,811,743 A | 3/1989 | Stevens | 128/772 |
| 4,835,003 A | 5/1989 | Becker et al. | 427/2 |
| 4,841,976 A | 6/1989 | Packard et al. | 128/657 |
| 4,867,174 A | 9/1989 | Skribiski | 128/772 |
| 4,884,579 A | 12/1989 | Engelson | 128/772 |
| 4,899,787 A | 2/1990 | Ouchi et al. | 138/131 |
| 4,922,924 A | 5/1990 | Gambale et al. | 128/772 |
| 4,925,445 A | 5/1990 | Sakamoto et al. | 604/95 |
| 4,955,862 A | 9/1990 | Sepetka | 604/164 |
| 4,961,731 A | 10/1990 | Bodicky et al. | 604/264 |
| 4,977,901 A | 12/1990 | Ofstead | 128/772 |
| 4,991,602 A | 2/1991 | Amplatz et al. | 128/772 |
| 5,045,072 A | 9/1991 | Castillo et al. | 604/280 |
| 5,061,254 A | 10/1991 | Karakelle et al. | 604/265 |
| 5,069,226 A | 12/1991 | Yamauchi et al. | 128/772 |
| 5,078,702 A | 1/1992 | Pomeranz | 604/280 |
| 5,095,915 A | 3/1992 | Engelson | 128/772 |
| 5,129,890 A | 7/1992 | Bates et al. | 604/281 |
| 5,178,158 A | 1/1993 | de Toledo | 128/772 |
| 5,333,620 A | 8/1994 | Moutafis et al. | 128/772 |
| 5,342,383 A | 8/1994 | Thomas | 606/190 |
| 4,739,768 A | 11/1994 | Engelson | 128/658 |
| 5,452,726 A | 9/1995 | Burmeister et al. | 128/772 |
| 5,606,981 A | 3/1997 | Tartacower et al. | 128/772 |
| 5,722,424 A | 3/1998 | Engelson | 128/772 |
| 5,749,837 A | 5/1998 | Palermo et al. | 600/585 |
| 5,769,796 A | 6/1998 | Palermo et al. | 600/585 |
| 5,772,609 A | 6/1998 | Nguyen et al. | 600/585 |
| 5,840,046 A | 11/1998 | Deem | 600/585 |
| 5,902,631 A | 5/1999 | Wang et al. | 427/2.1 |
| 5,924,998 A * | 7/1999 | Cornelius et al. | 600/585 |
| 6,251,086 B1 * | 6/2001 | Cornelius et al. | 600/585 |
| 6,306,105 B1 * | 10/2001 | Rooney et al. | 600/585 |

* cited by examiner

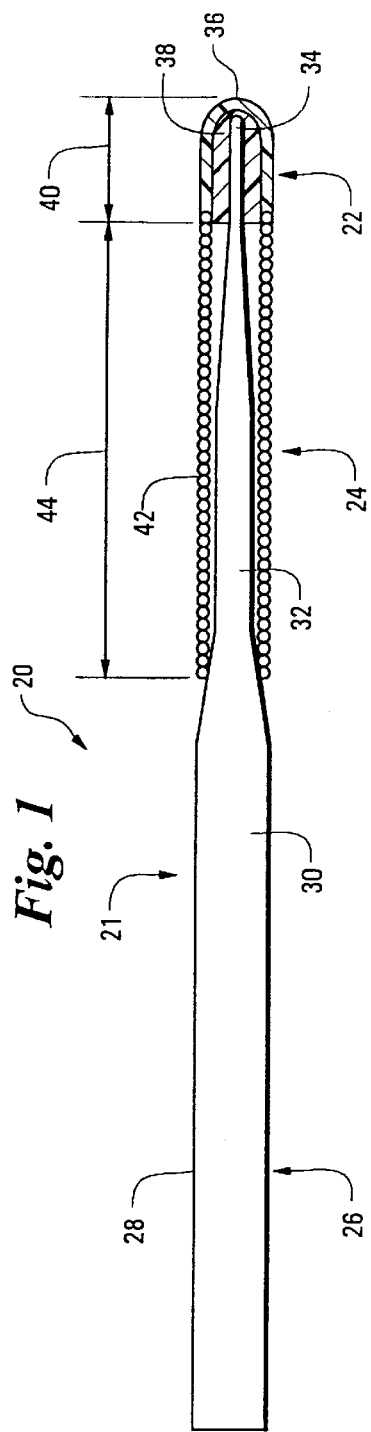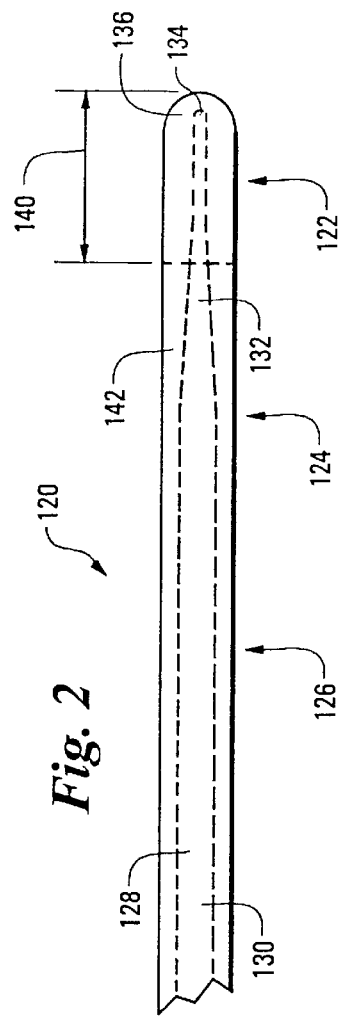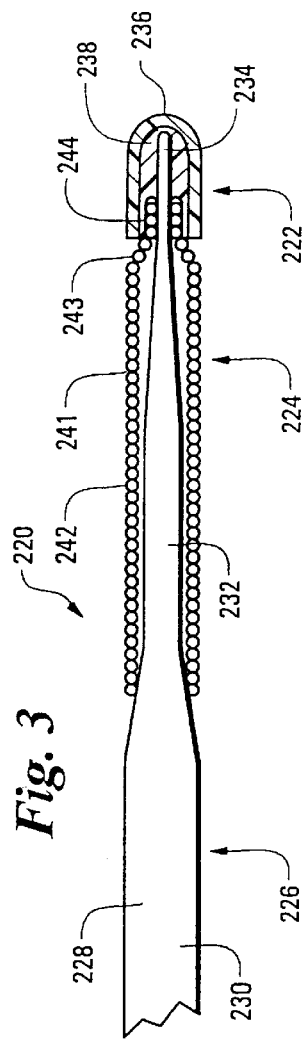

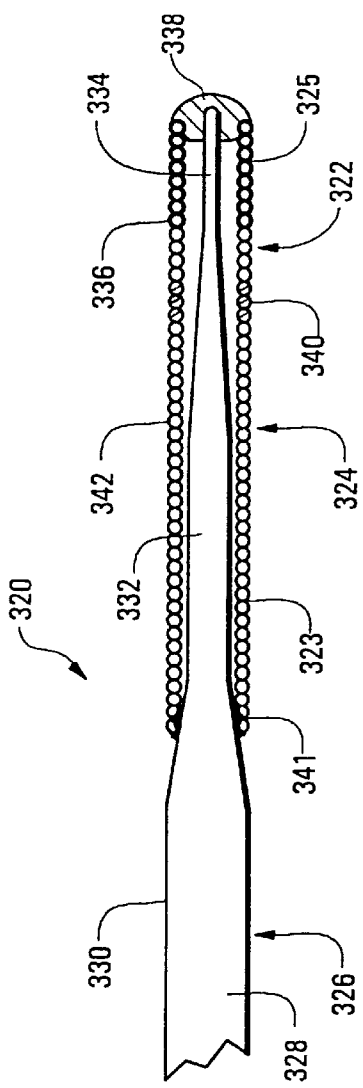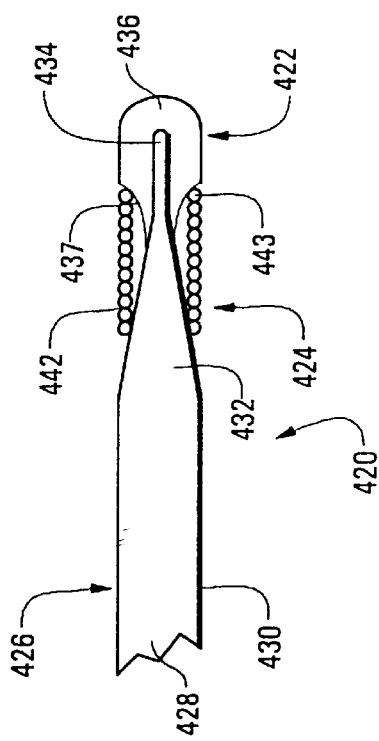

GUIDE WIRE WITH HYDROPHILICALLY COATED TIP

CROSS REFERENCE TO RELATED APPLICATIONS

This is a continuation of application Ser. No. 09/361,881 filed on Jul. 27, 1999, now U.S. Pat. No. 6,251,086, which continues application Ser. No. 08/812,750, filed on Mar. 6, 1997, now U.S. Pat. No. 5,924,998.

FIELD OF THE INVENTION

The present invention relates generally to intravascular guide wires. In particular, the present invention relates to guide wires having a lubricous hydrophilic tip and a less lubricous intermediate portion proximal the distal tip.

BACKGROUND OF THE INVENTION

Guide wires are used in various procedures within various conduits in the body. In particular, they are used in Percutaneous Transluminal Coronary Angioplasty (PCTA) and other coronary procedures. This can involve inserting a guide wire through an incision in the femoral artery near the groin, advancing the guide wire over the aortic arch, into a coronary artery, and across a lesion to be treated. Guide wires can be inserted directly into the vasculature or within a guide catheter. The distal end of the guide wire ultimately lies directly within the vasculature.

Guide wires serve to guide devices into position for both therapeutic and diagnostic purposes. For this to happen, the guide wire itself must be properly positioned. This is difficult, as it involves moving a wire tip through a narrow opening within a narrow vessel, from 180 centimeters away. This task can be especially difficult as the guide wire must be extremely flexible at the distal end to enable the guide wire tip to enter vessel branches at various angles. The extreme flexibility can come at the expense of axial or rotational strength. Improved responsiveness to remotely applied forces, both rotational and axial, has been provided by reducing friction along the guide wire length. In particular, providing a highly lubricous guide wire distal region of about 12 inches has proven advantageous in maneuvering guide wires through the arteries to reach the site of blockage. Having this same lubricous coating on the tip of the wire has been advantageous in making the wire perform better in finding small openings in the blockages and crossing them.

Once the guide wire tip is in position, devices including catheters are advanced into position over the guide wire and withdrawn over the guide wire. Such catheter movement acts upon, and tends to move, the guide wire contained within. This can tend to dislodge the guide wire tip. Minor patient movement including breathing also acts to move the guide wire as does handling of the guide wire proximal portion extending from the patient. Dislodging the guide wire tip may require repositioning the guide wire, with the attendant time and effort. Once in position, therefore, stability and resistance to applied forces is preferred over the initially desirable ease of movement and responsiveness to applied forces.

What is desirable and has not been provided is a guide wire easily maneuvered into position across a tight lesion, yet providing stability and resistance to movement once the guide wire is in position.

SUMMARY OF THE INVENTION

The present invention provides a guide wire having a highly lubricous distal portion, followed proximally by a less lubricous intermediate portion, followed proximally by a proximal portion. The guide wire includes a core member within, preferably formed of metal and having a proximal constant cross section portion, followed distally by a tapered portion, followed distally by a reduced cross section portion. The tapered portion can have multiple tapers. The distal end of the reduced cross section portion is preferably flattened into a ribbon, providing greater flexure in one plane. A preferred core has a circular cross section in the proximal and tapered portions. One guide wire embodiment has a intermediate and distal portion length totalling about 12 to 14 inches. A preferred length for the distal portion is about 1 to 3 centimeters.

A preferred guide wire achieves a lubricous distal portion by having a hydrophilic surface in the distal portion. A less lubricous intermediate portion is achieved by having a hydrophobic surface in the intermediate portion. The hydrophilic surface has a very low coefficient of friction when placed against an artery wall in a blood filled artery. The hydrophobic surface has a higher coefficient of friction against the artery wall.

The present invention distal portion can be formed of a polymer not necessarily hydrophilic, but having a hydrophilic coating thereover. The intermediate portion can be formed of a hydrophobic polymer sleeve over the core wire or a polymer sleeve over the core wire having a hydrophobic coating. In another embodiment, the intermediate portion can include a coil around the core wire, the coil preferably having a hydrophobic coating. The coil wire abuts the distal portion in one embodiment, and is embedded beneath the distal polymer in another embodiment. In yet another embodiment, the distal portion includes a distal tip having a proximally tapered proximal portion, and the coil wire distal end contacts the distal tip in the tapered portion, thereby centering the coil.

The present invention provides the ability to cross tight lesions by having a highly lubricous, low friction, distal portion, which is relatively easy to slide through a narrowed vessel region. The extremely lubricous portion is limited to a shorter length relative to previous devices. A preferred length is about 1 inch. The lubricity is limited to the portion where the extreme lubricity is most needed, the distal portion. Lower friction is required in the extreme distal portion because the core member there is narrower and therefore weaker, not having the strength of the more proximal portion to handle being axially pushed from the proximal end against obstructions. Low friction is also required in this portion because this is the portion that is required to initially cross an extremely tight lesion, something not required of the more proximal portion. The low friction facilitates the wire tip first piloting into the small remaining opening in the lesion and then crossing the lesion without buckling the wire.

To counteract the highly lubricous, low friction distal portion, the present invention deliberately provides a less lubricous, higher friction intermediate portion, proximal of the distal portion. The intermediate portion can lie against an artery wall, or guide catheter wall, "anchoring" the guide wire. The present invention, by having an anchoring portion proximal of the distal portion, provides resistance to forces such as catheter movement over the guide wire, which could act to dislodge the guide wire tip from its desired position.

While the anchoring portion friction will not prevent all movement of the guide wire, it provides sufficient static friction to resist unintentional movement due to either catheter movement or patient movement. In this way, a series of minor forces acting on the guide wire proximal portion, if below the threshold of static friction presented by the anchoring portion, will not be translated into a series of minor movements of the guide wire distal tip.

BRIEF DESCRIPTION OF THE DRAWINGS

FIG. 1 is a fragmentary, side cross-sectional view of a guide wire, in accordance with the present invention, having a coil in the intermediate portion;

FIG. 2 is a fragmentary, side cross-sectional view of a second embodiment of a guide wire having a core wire shown in phantom;

FIG. 3 is a fragmentary, side cross-sectional view of a third embodiment of a guide wire having a coil extending into the distal tip;

FIG. 4 is a fragmentary, side cross-sectional view of a fourth embodiment of a guide wire having a two part coil extending into the distal tip; and FIG. 5 is a fragmentary side cross-sectional view of a fifth embodiment of a guide wire having a proximally tapered polymer tip and a coil sitting on the taper.

DETAILED DESCRIPTION OF THE PREFERRED EMBODIMENTS

FIG. 1 illustrates a fragmentary, side cross-sectional view of a guide wire 20 having a distal portion 22, an intermediate portion 24, and a proximal portion 26. Guide wire 20 has a surface extending the length thereof, as indicated at 21. The length of distal portion 22 is indicated by arrows 40 and the length of intermediate portion 24 by arrows 44. Guide wire 20 includes an elongate core member 28 having a constant cross section portion 30, a tapered portion 32 and a reduced cross section portion 34. Core member 28 preferably has a circular cross section in portions 30 and 32. The intermediate tapered portion 32 may comprise a single taper or a series of tapers with regions of constant diameter in between. Core 28 is preferably formed from high tensile strength stainless steel wire or a super-elastic alloy such as Nitinol.

Core reduced cross section portion 34, illustrated lying within a distal portion 22, provides extreme flexibility to the guide wire where needed, at the extreme distal end. Reduced cross section portion 34 is preferably flatter in one dimension than another, forming a ribbon, providing more flexibility in one dimension than another. Tip flexibility is desirable for insinuating the guide wire into ever more distal and tortuous coronary arteries. The embodiment of distal portion 22 illustrated can include a distal tip 38 encasing core reduced cross section portion 34. In a preferred embodiment, distal tip 38 includes a polymeric material. Distal tip 38 is preferably radiopaque to allow for tracking the tip position using fluoroscopy. In one embodiment, tip 38 includes polyurethane and is loaded with tungsten, 85 to 90 percent by weight, for radiopacity. In one embodiment, a polyurethane sleeve forms distal tip 38, which can be between about ½ and 7 centimeters in length. In a preferred embodiment, tip 38 is between 1 and 3 centimeters in length.

Distal portion 22 according to the present invention is lubricous. In a preferred embodiment, distal portion 22 is extremely lubricous. In one embodiment, the lubricity is provided by having a hydrophilic material at the surface of distal portion 22. A hydrophilic surface makes the surface highly lubricous when in contact with a water based fluid such as blood. In the embodiment illustrated in FIG. 1, lubricity is provided by a distal layer 36 over reduced diameter portion 34 and distal tip 38. A hydrophilic coating over the guide wire presents very little friction when sliding through the artery interior. This provides ease of crossing tight lesions, allowing difficult and distally remote lesions to be treated. In one embodiment, distal layer 38 includes a polyvinylpyrrolidone (PVP) coating. In another embodiment, distal layer 38 includes a polyethyl maleic anhydride coating. In a preferred embodiment, distal portion 22 is about 0.014 inches in diameter.

Proximal of distal portion 22 is intermediate portion 24 which has a lubricity less than that of distal portion 22. In a preferred embodiment, intermediate portion 24 has length 44 of about 20 to about 30 centimeters. In one embodiment, intermediate portion 24 is about 28 centimeters long and about 0.0130 to 0.0135 inches in diameter. Guide wires used to deliver stiffer devices may have a shorter intermediate region to make the wire more supportive. In these cases intermediate portion 24 may be as short as 3 centimeters. In the embodiment depicted in FIG. 1, intermediate portion 24 includes tapered core portion 32 which is encased in a coil 42. A preferred coil is formed of stainless steel and coated with hydrophobic coating. A preferred hydrophobic coating is PTFE or silicone. Coil 42, by presenting a series of wires oriented transversely to the axial direction of guide wire movement, provides resistance to axial movement. The coil also provides increased pushability and kink resistance for tapered core portion 32. In compression, the coil provides axial strength over the length of tapered core portion 32 which decreases in strength with decreasing core cross section. The distal end of coil 42 can be attached to core 28 using solder or adhesive. The proximal end of coil 28 is preferably secured to core 28 by adhesive.

Intermediate portion 24 provides a higher friction anchoring portion to maintain the position of distal portion 22. If too much of the guide wire is extremely lubricous, the distal tip can be difficult to fix exactly in position, as catheter advancement and retraction over the guide wire can apply forces to the guide wire, tending to move the guide wire tip. Patient movement, including breathing, can also translate into movement at the guide wire distal tip. By providing an intermediate region having a less lubricous surface, an intermediate anchoring region is provided, which presents friction against the vessel wall, presenting resistance to forces that would otherwise be translated into movement at the distal tip. While the intermediate anchoring portion cannot resist all forces applied to the guide wire and prevent all tip movement, the static friction of the anchored guide wire intermediate portion does provide a threshold barrier to lower level forces. Thus, a series of small forces is not necessarily translated into a series of low level movements of the guide wire tip.

Proximal portion 26 in a preferred embodiment, extends to the guide wire proximal end. Included in proximal portion in FIG. 1 is constant cross section core portion 30. In a preferred embodiment, proximal portion 26 includes a stainless steel wire about 0.013 inches in diameter and has a polytetrafluoroethylene (PTFE) coating. In one embodiment, proximal portion 26 is less lubricous than intermediate portion 24. In another embodiment, proximal portion 26 is more lubricous than intermediate portion 24 but less lubricous than distal portion 22.

FIG. 2 illustrates another embodiment of the invention, guide wire 120, having a proximal portion 126, an intermediate portion 124, and a distal portion 122. Distal portion 122 is preferably about ½ to 7 centimeters in length, and intermediate portion 124 can be 1 to 15 inches in length and is preferably about 8 to 12 inches in length. Within guide wire 120 is a core 128 having a constant diameter portion 130, a tapered portion 132 and a reduced diameter portion 134. Core 128 can be substantially similar to core 28 discussed with respect to FIG. 1. Guide wire 120 has a lubricous distal portion 122 and a less lubricous intermediate portion 124. In the embodiment depicted in FIG. 2, distal portion 122 includes a distal tip 136. Distal tip 136 can be similar to distal tip 36 in FIG. 1. In some embodiments, distal tip 136 is formed of polyurethane, and coated with hydrophilic coatings as discussed above with respect to FIG. 1. Distal tip 136 is preferably radiopaque to allow for tracking the tip position using fluoroscopy. In one embodiment, tip 136 includes polyurethane and is loaded with tungsten, 85 to 90 percent by weight, for radiopacity. Distal tip 136 is preferably more radiopaque than intermediate portion 124.

Intermediate portion 124 provides a less lubricous portion proximal to lubricous distal portion 122, as in the embodiment of FIG. 1, but without requiring a coil. The lower lubricity is provided by having a hydrophobic surface. This can be provided with both hydrophobic sleeves and hydrophobic coatings over sleeves that are not necessarily hydrophobic. Sleeve 142, illustrated encasing tapered core portion 132, can be formed of a hydrophobic polymer. Hydrophobic polymers include fluorinatedethylenepropylene (FEP) and polytetrafluoroethylene (PTFE). Intermediate portion 124 can also be formed of a material such as polyether block amide (PEBAX) or polyethylene coated with a low friction, hydrophobic coating such as silicone, paralene, PTFE, or FEP. Guide wire 120 can be formed by sleeving tube 142 over core 128, bonding the tube in place at its proximal end with adhesive, shrinking a suitable distal tip material over reduced diameter core portion 134, and bonding the distal portion of sleeve 142 to the proximal portion of the distal tip. Another suitable method includes heat shrinking a polymeric tube over core 128, grinding the tube to an approximate diameter of about 0.0130 to 0.0135 inches, then selectively coating intermediate portion 124 and possibly distal portion 122 also, with one of the hydrophobic coatings, and then coating distal portion 122 with one of the previously described hydrophilic coatings.

FIG. 3 illustrates yet another embodiment of the invention, a guide wire 220, having proximal portion 226 followed distally by intermediate portion 224 followed distally by distal portion 222. A core 228 proceeds distally from a constant diameter portion 230 to a tapered portion 232 to a reduced diameter portion 234. Intermediate portion 224 includes a coil 242 surrounding the tapered portion of the core, with coil 242 proceeding distally from a constant diameter portion 241 to a tapered portion 243 to a reduced diameter portion 244. Core 228 is preferably flattened into a ribbon shape in reduced diameter portion 244. Reduced diameter portion 244 is embedded within distal tip 238 when the polymer tip is shrunk onto the wire. In this embodiment, neither solder nor adhesive are required to secure the distal end of coil 242 to core 228. The proximal end of coil 242 can be secured to core 228 by soldering. Distal tip 238 can be coated with a hydrophilic layer 236 as discussed above with respect to the embodiment of FIG. 1. The materials of distal tip 238 and layer 236 can be similar to those of distal tip 38 and layer 36.

FIG. 4 illustrates yet another embodiment of the invention, a guide wire 320, having a proximal portion 326, followed by an intermediate portion 324, followed distally by a distal portion 322. A core 328 proceeds distally from a constant diameter portion 330 to a tapered portion 332, to a reduced diameter portion 334. A coil 342 surrounds core 328 over the intermediate and distal portions. In the embodiment shown, coil 342 is formed of a proximal coil 323 and a distal coil 325 soldered together at 340. Proximal coil 323 is preferably formed from a less radiopaque material such as stainless steel. This coil can be coated with a hydrophobic coating such as PTFE. Distal coil 325 is preferably formed of a more radiopaque material such as platinum. Combined coil 342 is attached to core 328 proximally with solder at 341 and distally with either solder or welding at 338. A hydrophilic coating 336 is applied to the distal portion of distal coil 325 in one embodiment by first applying a Tie layer polymer such as polyurethane by dip or spray coating, followed by applying a hydrophilic coating over the Tie layer coating. The hydrophilic coating can be one of the coatings described previously with respect to guide wire 20 in FIG. 1.

FIG. 5 illustrates yet another embodiment of the invention, a guide wire 420 having a proximal portion 426, followed by an intermediate portion 424, followed distally by a distal portion 422. A core 428 proceeds distally from a contact diameter portion 430 to a tapered portion 432, to a reduced diameter portion 434. A distal tip 436, preferably formed of a polymeric substance, surrounds core reduced diameter distal portion 434. Distal tip 436 includes a tapered portion 437, which tapers proximally toward core tapered portion 432. Guide wire 420 includes a coil 442 which extends distally over core tapered portion 432. Coil 442 has a distal end 443 which contacts and terminates within distal tip tapered portion 437. Coil 442 is thus always centered on core 428, as transverse movement of coil distal end 443 is opposed by distal tip tapered portion 437. Tip 436 can be heated to embed end 443 therein.

While use of the present invention can be described with reference to any of the embodiments, the embodiment of FIG. 1 is selected for further illustration. In use, core reduced diameter portion 34 can be bent by the treating physician, prior to insertion into the patient. Having a bent distal tip allows orienting the tip for insertion into arteries by rotating the proximal end of the guide wire, which rotates the bent distal tip toward arterial side branches. The guide wire can be advanced through a guide catheter or directly through the vasculature. After having advanced the guide wire into a coronary artery such as the left coronary artery, the guide wire is maneuvered into selected smaller arteries. In attempting to insinuate the distal most portion of the guide wire into smaller arteries, the lubricous tip provides easier initial advancement into the artery. When a lesion is to be crossed, lubricous distal portion 22 provides low resistance to axial movement into and through a narrow passage. Low resistance is advantageous as there is less tendency for core reduced diameter portion 34 to kink or buckle when pushed by the treating physician from the extreme proximal end.

Once distal portion 22 is across the lesion, it is highly preferred that the guide wire tip position not change, despite minor changes in proximal handling of the guide wire, movement of other devices over the guide wire, patient breathing, blood flow, and minor changes in frictional conditions along the guide wire length. The present invention allows a guide wire to resist these forces by having intermediate portion 24 lie against and be "anchored" to the vessel or guide catheter wall, presenting a higher quantity of static friction that must be overcome to dislodge the guide wire distal tip, than presented with wires having longer lubricous distal surfaces. The present invention thus makes it less likely that the guide wire will move inside the artery unless the physician is directly intending to move it.

The combination of lubricous distal portion and less lubricous intermediate portion thus serves to promote ease of distal tip advancement across tight lesions while stabilizing the distal tip position once placed, allowing other devices to be accurately guided into position by the guide wire.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A guidewire having a distal end and a proximal end, comprising:
    an elongate core;
    a distal portion including a hydrophilic surface;
    an intermediate portion proximal of said distal portion, said intermediate portion including a hydrophobic surface having a coefficient of friction greater than said hydrophilic surface; and
    a proximal portion proximal of said intermediate portion.

2. The guidewire of claim 1, wherein said proximal portion includes a surface.

3. The guidewire of claim 2, wherein said proximal portion surface is a hydrophobic coating.

4. The guidewire of claim 3, wherein said hydrophobic coating is polytetrafluoroethylene.

5. The guidewire of claim 3, wherein said proximal portion surface is less lubricious than said distal portion surface but more lubricious than said intermediate portion surface.

6. The guidewire of claim 1, wherein said hydrophilic surface is a polyvinylpyrrolidone coating.

7. The guidewire of claim 1, wherein said hydrophilic surface is a polyethyl maleic anhydride coating.

8. The guidewire of claim 1, further comprising a coil disposed about the elongate core at said intermediate portion.

9. The guidewire of claim 8, wherein said coil is encased within said hydrophobic surface.

10. The guidewire of claim 1, wherein the proximal portion has a level of lubriciousness different from that of the intermediate portion.

11. A guidewire of having a distal end and a proximal end, comprising:
    an elongate core;
    a distal portion including a hydrophilic surface;
    an intermediate portion proximal of said distal portion, said intermediate portion including a hydrophobic surface having a coefficient of friction greater than said hydrophilic surface;
    a proximal portion proximal of said intermediate portion; and
    a coil disposed about the elongate core at said intermediate and distal portions;
    wherein said coil comprises a proximal portion formed of a radiotransparent material, and a distal portion formed of a radiopaque material.

12. The guidewire of claim 11, wherein said radiotransparent material is stainless steel.

13. The guidewire of claim 11, wherein said radiopaque material is platinum.

14. A guidewire having a distal end and a proximal end, comprising:
    an elongate core;
    a distal portion including a hydrophilic surface;
    an intermediate portion proximal of said distal portion, said intermediate portion including a hydrophobic surface having a coefficient of friction greater than said hydrophilic surface; and
    a coil disposed about the elongate core at said intermediate portion.

15. The guidewire of claim 14, wherein the proximal portion has a level of lubriciousness different from that of the intermediate portion.

* * * * *